(12) United States Patent
Su et al.

(10) Patent No.: US 8,648,731 B2
(45) Date of Patent: Feb. 11, 2014

(54) GAS CONCENTRATION MONITOR

(75) Inventors: Leilong Su, Nanjing (CN); Feng Qian, Nanjing (CN); Yanqi Li, Nanjing (CN)

(73) Assignee: Empire Technology Development LLC, Wilmington, DE (US)

( * ) Notice: Subject to any disclaimer, the term of this patent is extended or adjusted under 35 U.S.C. 154(b) by 197 days.

(21) Appl. No.: 13/132,080

(22) PCT Filed: Jun. 9, 2010

(86) PCT No.: PCT/CN2010/073695
§ 371 (c)(1),
(2), (4) Date: Jun. 1, 2011

(87) PCT Pub. No.: WO2011/153687
PCT Pub. Date: Dec. 15, 2011

(65) Prior Publication Data
US 2011/0304470 A1    Dec. 15, 2011

(51) Int. Cl.
*G08B 17/10* (2006.01)
*G01N 21/59* (2006.01)

(52) U.S. Cl.
USPC ............ 340/632; 340/630; 340/634; 356/437

(58) Field of Classification Search
USPC .................... 340/632, 633, 634, 541, 630; 250/338.1, 339.02, 573; 356/436, 437, 356/439; 385/12, 16, 140; 398/83; 372/10, 372/20, 21
See application file for complete search history.

(56) References Cited

U.S. PATENT DOCUMENTS

| | | | |
|---|---|---|---|
| 5,767,976 A | 6/1998 | Ankerhold et al. | |
| 6,816,517 B2 * | 11/2004 | Jacobowitz et al. | ............ 372/20 |
| 7,075,653 B1 | 7/2006 | Rutherford | |
| 7,136,588 B1 * | 11/2006 | Islam et al. | ...................... 398/83 |
| 7,145,455 B2 * | 12/2006 | Eskildsen et al. | ............. 340/541 |
| 7,218,222 B2 * | 5/2007 | Eskildsen et al. | ............. 340/541 |
| 7,312,452 B2 | 12/2007 | Klingenberg et al. | |
| 7,409,117 B2 * | 8/2008 | Von Drasek et al. | ............. 385/12 |
| 7,683,357 B2 * | 3/2010 | Von Drasek et al. | .......... 250/573 |
| 2007/0164221 A1 | 7/2007 | Russell | |
| 2008/0231857 A1 * | 9/2008 | Depeursinge et al. | ........ 356/437 |

FOREIGN PATENT DOCUMENTS

| | | |
|---|---|---|
| CN | 101042340 A | 9/2007 |
| GB | 2181536 A | 4/1987 |
| JP | 2000241313 A | 9/2000 |

(Continued)

OTHER PUBLICATIONS

Notification of Transmittal of the International Search Report and the Written Opinion of the International Searching Authority, Mar. 24, 2011.

(Continued)

*Primary Examiner* — Van T. Trieu
(74) *Attorney, Agent, or Firm* — Ren-Sheng International

(57) ABSTRACT

Techniques are generally described related to a method and system for monitoring gas concentrations. One example gas monitoring apparatus includes a light source, a MEMS micromirror arranged to be in an optical path of a light from the light source that has passed through a sample and configured to direct selected wavelengths of the light to a single detection point, a detector arranged at the single detection point and configured to convert incident light into electrical signals, and a processor programmed to determine a gas concentration of one or more gases in the sample based on the electrical signals.

20 Claims, 2 Drawing Sheets

(56) References Cited

FOREIGN PATENT DOCUMENTS

| JP | 2005121463 A | 5/2005 |
| JP | 2005156329 A | 6/2005 |
| JP | 2008116469 A | 5/2008 |
| JP | 2008232918 A | 10/2008 |
| WO | 2001077628 A1 | 10/2001 |

OTHER PUBLICATIONS

"ECO SCAN: ESS111A Product Spec", printed on Feb. 12, 2009, Nippon Signal.

* cited by examiner

GAS CONCENTRATION MONITOR

CROSS-REFERENCE TO RELATED APPLICATIONS

The present application is a 371 application of the International Application PCT/CN2010/073695, filed on Jun. 9, 2010 and entitled "Gas Concentration Monitor." The International Application, including any appendices or attachments thereof, is incorporated by reference herein in its entirety.

TECHNICAL FIELD

The present disclosure relates generally to gas concentration monitoring techniques.

BACKGROUND

Unless otherwise indicated herein, the approaches described in this section are not prior art to the claims in this application and are not admitted to be prior art by inclusion in this section.

Gas detectors, particularly gas detectors capable of reliably quantifying gas concentration of one or more gases, have many useful applications in industrial, research, and other settings. For example, any combustible gas, e.g., methane, hydrogen, etc., has a lower explosive limit and an upper explosive limit associated therewith, and any time the concentration in the air of a combustible gas falls between its upper and lower explosive limits, an explosion can occur with any spark. Such explosions can result in loss of life, destruction of industrial facilities, interruption of production, and secondary disasters, such as dust explosions, mine fires, and mine collapse.

SUMMARY

In accordance with one embodiment of the disclosure, a gas monitoring apparatus includes a light source, a MEMS micro-mirror arranged to be in an optical path of a light from the light source that has passed through a sample and configured to direct selected wavelengths of the light to a single detection point, a detector arranged at the single detection point and configured to convert incident light into electrical signals, and a processor programmed to determine a gas concentration of one or more gases in the sample based on the electrical signals.

In accordance with another embodiment of the disclosure, a method for determining a gas concentration in a gas sample includes transmitting a light through the gas sample, separating the transmitted light into a plurality of wavelengths, directing selected wavelengths of the light transmitted through the gas sample to a single detection point, and determining the gas concentration based on signals generated from the selected wavelengths detected at the single detection point.

In accordance with a further embodiment of the disclosure, an alarm system for protection from high concentration of certain gases includes a gas concentration monitoring device, a processor, and an alarm. The gas concentration monitoring device includes a MEMS micro-mirror that directs selected wavelengths of a light, which has been transmitted through a sample that is being monitored for harmful gases, to a single detection point, and a detector arranged at the single detection point that converts incident light into electrical signals. The processor that determines a gas concentration of one or more gases in the sample based on the electrical signals, and the alarm is generated when the gas concentration of a certain gas exceeds a threshold.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
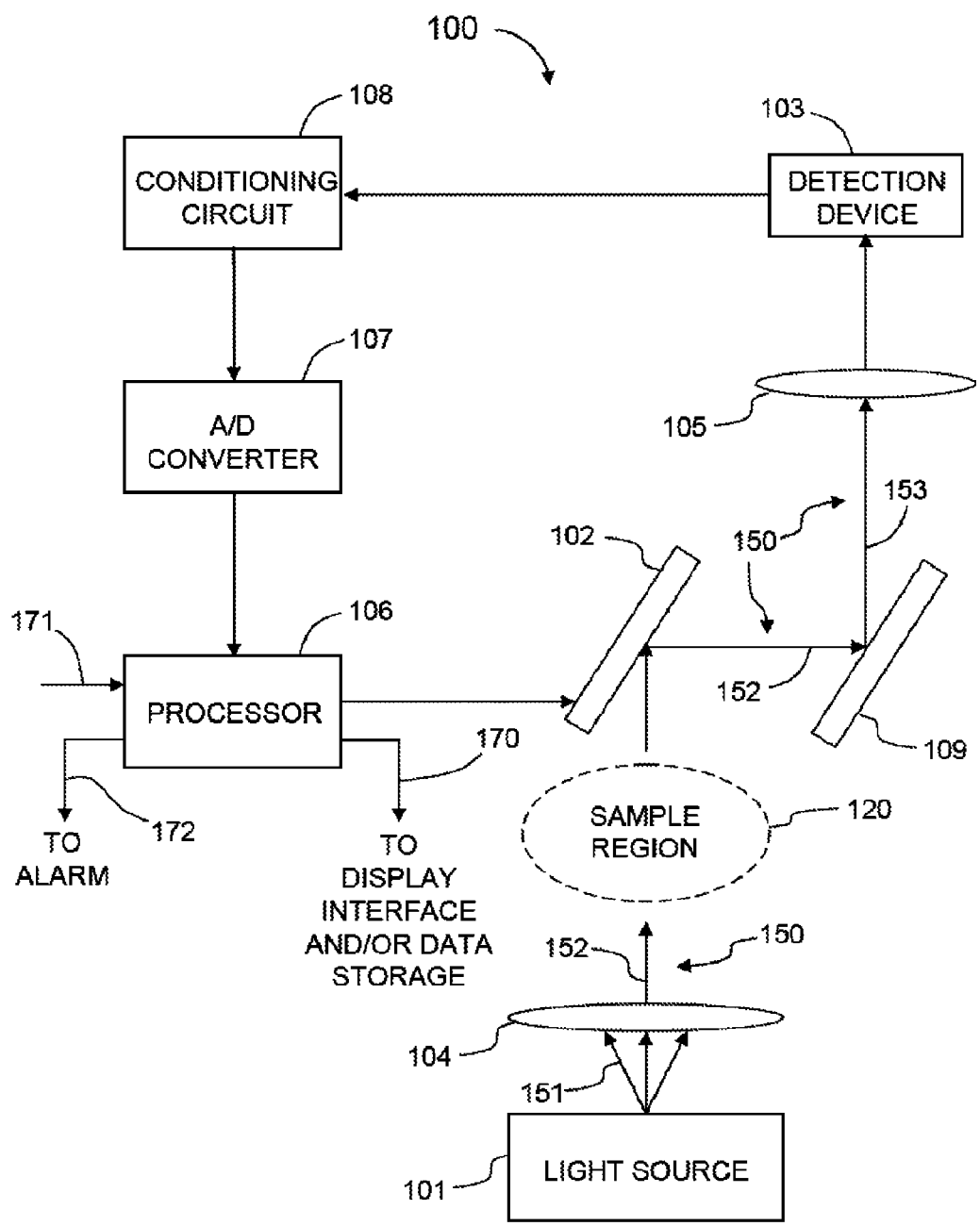
FIG. 1 shows a schematic diagram of an illustrative embodiment of a gas monitoring apparatus with an optical path.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to techniques, methods, and apparatuses related to monitoring gas concentrations.

When light is transmitted through a gas sample or when light is incident on a thin disk of a solid material, molecules contained in the material selectively absorb the transmitted light at specific, unique frequency bands, or absorption lines. These absorption lines are evident in the spectrum of the light that results after the light has been transmitted through the material. This resultant spectrum is more commonly known in the art as the material's "absorption spectrum." Based on Lambert-Beer's theorem and chemometrics techniques known in the art, the relationship between absorbance of certain frequency bands and the concentration of a gas can be derived for a particular gas or gas mixture, enabling qualitative and quantitative analysis of the gas sample. The absorption spectrum of a gas molecule due to the fundamental vibration of the molecule often lies in the middle infrared band, i.e., light having a wavelength of about 400-4000 $cm^{-1}$, and the absorption spectrum of doubled and compound frequencies lies in the near infrared band, i.e., light having a wavelength of about 4000-14285 $cm^{-1}$, or about 2500-700 nm. Methane, the principle component of natural gas, has a near-infrared absorption peak at around the 1650 nm wavelength. Therefore, gas concentration detection can be conducted in the near-infrared wavelength range for methane, according to embodiments disclosed herein.

Embodiments disclosed herein contemplate a gas monitoring apparatus capable of accurately and reliably determining the concentration of one or more gases in a gas sample. The gas monitoring apparatus includes a light source, a single light sensor, a diffraction grating, and a microelectromechanical system (MEMS) scanning micro-mirror that serves as a scanning raster. Because the MEMS scanning micromirror can be precisely rotated or positioned in response to a control signal, each desired wavelength of light from the absorption spectrum of the gas sample may be selectively directed to the light sensor, thereby enabling full-spectrum acquisition of the absorption spectrum of the gas sample with a single light sensor. Full-spectrum acquisition of the absorption spectrum of the gas sample, in conjunction with any of the chemometrics techniques known in the art, allows for the accurate gas monitoring of one or more gases contained in the gas sample with the single light sensor.

FIG. 1 shows a schematic diagram of an illustrative embodiment of a gas monitoring apparatus 100 with an optical path 150. As depicted, gas monitoring apparatus 100 includes a light source 101, a MEMS scanning micro-mirror 102, a blazed grating 109, a single point detection device 103, a collimating optical element 104, a focusing optical element 105, a processor 106, an analog-to-digital (A/D) converter 107 and a conditioning circuit 108, which may be arranged as shown. Optical path 150 indicates the path by which light from light source 101 travels through a sample region 120 to single point detection device 103 during operation of gas monitoring apparatus 100.

Light source 101 may be a halogen, LED, or other light source that provides a broadband source of light for transmission through a sample gas located or contained in sample region 120. The particular light source may be selected based on the wavelengths occupied by the absorption lines in the absorption spectrum of the gas sample. For example, for a gas sample containing methane, which has an absorption peak in the near-infrared wavelength range, incandescent or quartz halogen bulbs may be used as broadband sources of near-infrared radiation. MEMS scanning micro-mirror 102 may be a digitally driven, MEMS-based optical scanning micro-mirror, and directs light that has passed through sample region 120 to blazed grating 109. By quickly rotating to one or more specified angles, MEMS scanning micro-mirror 102 may be configured to repeatedly direct light that has passed through sample region 120 across a desired portion of blazed grating 109. A MEMS-based optical scanning micro-mirror suitable for use as MEMS scanning micro-mirror 102 in gas monitoring apparatus 100 is the ESS111A optical scanning micro-mirror, available from Japan Signal Company, located in Tokyo, Japan. Blazed grating 109 serves as a diffraction grating for gas monitoring apparatus 100. Blazed grating 109 is configured to spatially separate the wavelength elements of the collimated incident light and to produce maximum efficiency at a specified wavelength. Single point detection device 103 converts incident light into electrical signals. In some embodiments, single point detection device 103 is an InGaAs single point detection device. However, other similar light detection devices known in the art, such as PbS-, Ge-, or Si-based devices, may be used as single point detection device 103. Collimating optical element 104 may be a mirror, lens system, or other optical element configured to collimate incident light from monochromatic light source 101 and direct the collimated light to MEMS scanning micro-mirror 102. Focusing optical element 105 may be a mirror, lens system, or other optical element configured to focus and direct light from blazed grating 109 to single point detection device 103. Processor 106 may be used to position MEMS scanning micro-mirror 102, control a temperature control circuit (not shown) as appropriate, perform signal acquisition from ND converter 107, process received data, and control a display interface (not shown). In some embodiments, processor 106 may be a single-chip processor such as the C8051F single-chip microcomputer, available from Silicon Labs located in Austin, Tex. Conditioning circuit 108 filters and amplifies the signal produced by single point detection device 103 for analog-to-digital conversion. A/D converter 107 performs the analog-to-digital conversion of the signal from conditioning circuit 108.

In one embodiment, gas monitoring apparatus 100 is configured to monitor the concentration of methane gas, a configuration that may be used in mines to aid in the prevention of explosions. In such an embodiment, single point detection device 103 operates in the long-wave near-infrared band to measure the absorption spectrum of methane. In addition, because methane is a combustible gas, gas monitoring apparatus 100 may be configured in accordance with explosion-proof requirements known in the art, such as having a high-strength casing. Suitable alarm displays may also be incorporated into gas monitoring apparatus 100, which are activated whenever methane concentrations are close to or exceed predetermined safety thresholds.

When gas monitoring apparatus 100 is in operation, a sample gas is introduced into sample region 120, and light source 101 directs light of a selected wavelength band through sample region 120. Light rays 151, which may originate from a point source, i.e., a source of radially divergent light rays, are collimated by collimating optical element 104 to form a collimated beam 152. Collimated beam 152 passes through the gas sample for a known distance, for example, about 10 cm. The length of sample region 120, i.e., the distance that collimated beam 152 travels through the sample gas, may vary depending on the light intensity and the sensitivity of single point detection device 103. Collimated beam 152 is then incident on MEMS scanning micro-mirror 102. While collimated beam 152 passes through the gas sample, one or more of the gases contained in the gas sample selectively absorb light at certain known frequency bands. Consequently, upon leaving sample region 120, collimated beam 152 includes the absorption spectrum (or spectra) unique to the gas (or gases) contained in the gas sample, and is directed to MEMS scanning micro-mirror 102. Controlled by processor 106, MEMS scanning micro-mirror 102 rotates to one or more angles to direct collimated beam 152 to one or more portions of blazed grating 109, where the one or more portions of blazed grating 109 that are illuminated may depend on the wavelength or wavelengths of wavelength components 153. Blazed grating 109 spatially separates the constituent wavelengths of light making up collimated beam 152 via diffraction. As collimated beam 152 is scanned across the surface of blazed grating 109, full-range, point-wise scanning of the incident light is performed, thereby selectively directing a single desired wavelength component 153 of collimated beam 152 to focusing optical element 105. Thus, as MEMS scanning micro-mirror 102 scans collimated beam 152 across a different portion of blazed grating 109, a different wavelength component 153 of collimated beam 152 may be directed to focusing optical element 105. Focusing optical element 105 focuses the incident light, i.e., wavelength component 153, on single point detection device 103. Single point detection device 103 converts incident light into electrical signals, and conditioning circuit 108 filters and amplifies these electrical signals for A/D conversion by A/D converter 107. The electrical signals produced by single point detection device 103 may be analog electrical signals proportionate in amplitude to the intensity of light entering single point detection device 103. Processor 106 receives the digital signals from A/D converter 107 and may process the received data (i.e., digital signals) using any of a variety of chemometric techniques known in the art to determine the gas concentration of the sample gas, represented by gas concentration data 170 in FIG. 1. Gas concentration data 170 generated by processor 106 may be displayed real-time on a display interface and/or stored for further analysis and long-term process monitoring. In addition, processor 106 may compare the current gas concentration of the sample gas to a gas concentration safety threshold 171, which may be specified by a user. Whenever the current gas concentration of the sample gas exceeds gas concentration safety threshold 171, processor 106 may cause an alarm signal 172 to be output to an alarm display or an audio alarm unit.

The scanning process performed by MEMS scanning micro-mirror 102 enables the use of a single light detection device, i.e., single point detection device 103, to quantify the absorption spectrum of a gas sample, rather than an array of detection devices. This is because MEMS scanning micro-mirror 102, in conjunction with blazed grating 109, can perform full bandwidth scanning in a desired band, i.e., MEMS scanning micro-mirror 102 can be rotated to direct light to various regions of blazed grating 109, so that light at various wavelengths in the covered range can be measured by single point detection device 103. And, unlike a spectrophotometer that relies on a fixed array of multiple light detectors, the desired band or bands measured by gas monitoring apparatus 100 may be selected to facilitate monitoring of the concentration of a variety of gases and gas mixtures. In addition, the use of scanning micro-mirror grating technology, i.e., MEMS scanning micro-mirror 102, ensures high efficiency and performance. First, the precision of the MEMS manufacturing process can effectively eliminate scanning noise. Second, the drive circuit is simple and easy to tune, since the driving signal from processor 106 is directly applied to MEMS scanning micro-mirror 102.

Traditional gas monitors are primarily based on electrochemical sensors, which have a limited lifetime due to degradation of sensor precision and accuracy. Loss of accuracy over time is a serious safety concern when such sensors are used to monitor combustible gases, e.g., in coal mines, and a serious process control issue when such sensors are used for long-term monitoring of a chemical process. Other gas sensing technologies are also known in the art, but are subject to other drawbacks. For example, a filter-based near-infrared spectroscope has a simple structure and small size and is relatively easy to manufacture. However, such instruments suffer from low accuracy and the ability to monitor only a limited number of gases. A Fourier-based instrument has high precision, good repeatability, and reliability, but the core component, the interferometer, is large, expensive, and can be extremely sensitive to vibration, making use in an industrial setting problematic. An acousto-optic, tunable apparatus has high precision without moving parts, but the frequency sensitive band is limited. A detector array uses a raster as a grating, and has a fast response with no moving parts, but array detectors working in the long-wave near-infrared band are very expensive and complex.

In contrast, various embodiments of the disclosure, as described herein, may be based on a single light sensor and a MEMS scanning micro-mirror. In addition, with a MEMS scanning micro-mirror, the stability of the optical path is ensured, and portability is readily achieved by miniaturization of the components. Various embodiments of the disclosure are also capable of high analysis resolution, and can generate data within a few seconds. Such real-time monitoring is highly beneficial for monitoring combustible gases, industrial emissions, and critical manufacturing processes. For example, in the event of a sudden increase in combustible gas content, a gas monitoring device, configured according to embodiments of the disclosure, can alarm immediately, and measures can be taken to gain valuable time for saving lives and property.

Figure 2:
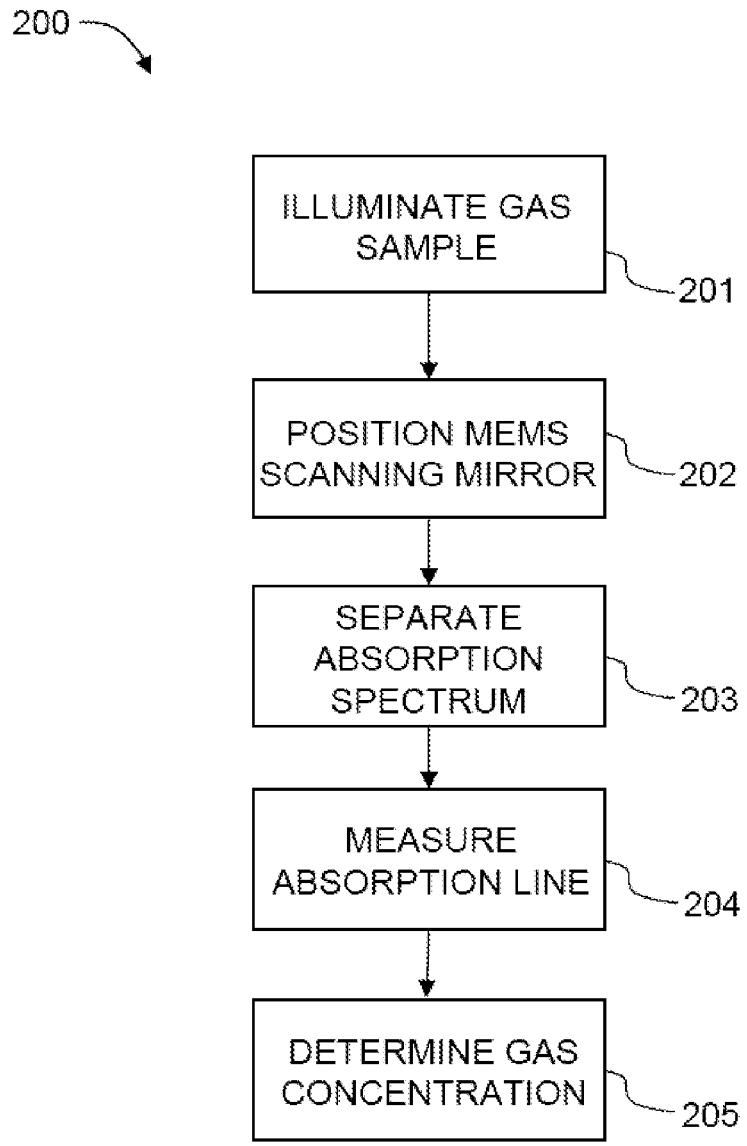
FIG. 2 is a flow chart of an illustrative embodiment of a method for monitoring gas concentration.

FIG. 2 is a flow chart of an illustrative embodiment of a method 200 for monitoring gas concentration. For ease of description, method 200 is described in terms of operation of a gas monitoring apparatus substantially similar to gas monitoring apparatus 100 in FIG. 1. However, other configurations of gas monitoring apparatuses may also perform method 200. Method 200 may include one or more operations, functions, or actions as illustrated by blocks 201, 202, 203, 204, and/or 205. The various blocks are not intended to be limiting to the described embodiments. For example, one skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In block 201 (ILLUMATE GAS SAMPLE), a gas sample is illuminated by light source 101 to produce an absorption spectrum in the light that passes through the gas sample. The light is then directed to MEMS scanning micro-mirror 102 by suitable optical elements, such as collimating optical element 104.

In block 202 (POSITION MEMS SCANNING MIRROR), MEMS scanning micro-mirror 102 directs light that has passed through sample region 120 to blazed grating 109. Processor 106 positions MEMS scanning micro-mirror 102 to direct incident light to a specified portion of blazed grating 109, so that a specific absorption line of the gas sample absorption spectrum may be analysed in block 204.

In block 203 (SEPARATE ABSORPTION SPECTRUM), blazed grating 109 spatially separates the wavelength components of incident light. The wavelength of light that is produced depends on what portion of blazed grating 109 is illuminated. Thus, a desired absorption line can be produced by illuminating a specific portion of blazed grating 109.

In block 204 (MEASURE ABSORPTION LINE), the desired absorption line of the gas sample absorption spectrum is received by single point detection device 103. The absorption lines may be focused by focusing optical element 105 en route to single point detection device 103. Single point detection device 103 converts the received optical energy into electrical signals that are received by processor 106 as digital data. If additional absorption lines of the gas sample absorption spectrum are required in order to perform accurate analysis of the gas sample, block 203 is repeated for each absorption line.

In block 205 (DETERMINE GAS CONCENTRATION), processor 106 processes the received data using any one of a variety of chemometric methods known in the art to determine the concentration of the target gas in the gas sample. Processor 106 may optionally compare the current gas concentration of the gas sample to a predetermined gas concentration safety threshold to further determine if an alarm condition has occurred. Processor 106 may then output the gas concentration data to a display interface and/or to data storage and, if applicable, output an alarm condition to a suitable alarm display.

There is little distinction left between hardware and software implementations of aspects of systems; the use of hardware or software is generally (but not always, in that in certain contexts the choice between hardware and software can become significant) a design choice representing cost vs.

efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A gas monitor apparatus comprising:
a light source configured to generate a light;
a blazed grating including one or more positions configured to separate the light into one or more selected wavelengths of the light;
a MEMS micro-mirror arranged to be in an optical path of the light from the light source that has passed through a sample, wherein the MEMS micro-mirror is configured to direct the light to a first position on the blazed grating to generate a first of the selected wavelengths of the light, and direct the first of the selected wavelengths of the light to a single detection point;
a detector arranged at the single detection point and configured to convert the first of the selected wavelengths of the light into electrical signals; and
a processor programmed to determine a gas concentration of one or more gases in the sample based on the electrical signals.

2. The gas monitor apparatus of claim 1, wherein the MEMS micro-mirror is configured to direct the light to a second position on the blazed grating to generate a second of the selected wavelengths of the light.

3. The gas monitor apparatus of claim 2, wherein each of the selected wavelengths of the light corresponds to an absorption spectrum of one or more gases in the sample that are to be monitored.

4. The gas monitor apparatus of claim 1, wherein the detector includes an InGaAs single point detection device.

5. The gas monitor apparatus of claim 1, further comprising a collimator optical element arranged in the optical path of the light between the light source and the MEMS micro-mirror.

6. The gas monitor apparatus of claim 1, further comprising a focus optical element arranged in the optical path to focus the selected wavelengths of the light that are directed by the MEMS micro-mirror onto the single detection point.

7. The gas monitor apparatus of claim 1, wherein the light source includes a broadband light source.

8. A method to determine a gas concentration in a gas sample, comprising:
transmitting a light through the gas sample;
rotating a MEMS micro-mirror to direct the transmitted light to one or more positions on a blazed grating to separate the transmitted light into one or more selected wavelengths;
directing the selected wavelengths of the light separated by the blazed grating to a single detection point; and
determining the gas concentration based on signals generated from the selected wavelengths detected at the single detection point.

9. The method of claim 8, further comprising:
detecting the selected wavelengths at the single detection point and generating electrical signals therefrom,
wherein the gas concentration is determined based on the electrical signals.

10. The method of claim 8, further comprising:
selecting the one or more wavelengths of the transmitted light to be monitored,
wherein the directing includes controlling the MEMS micro-mirror to direct each of the selected wavelengths to the single detection point.

11. The method of claim 10, wherein the selected wavelengths of the light correspond to an absorption spectrum of the gas sample.

12. The method of claim 8, further comprising:
collimating the transmitted light prior to separating.

13. The method of claim 8, wherein directing the selected wavelengths of the light to the single detection point includes:
focusing the selected wavelengths of the transmitted light to the single detection point.

14. The method of claim 8, further comprising:
generating the light from a broadband light source,
wherein the transmitting the light through the gas sample includes transmitting the light generated from the broadband light source through the gas sample.

15. An alarm system for protection from high concentration of certain gases, comprising:
a gas concentration monitor device including:
a blazed grating including one or more positions configured to generate one or more selected wavelengths of a light,
a MEMS micro-mirror that is configured to direct the light, which has been transmitted through a sample that is to be monitored for harmful gases, to one of the positions on the blazed grating to generate one of the selected wavelengths of the light, and direct the generated one of the selected wavelengths of the light to a single detection point,
a detector, arranged at the single detection point, to convert incident light into electrical signals, and
a processor to determine a gas concentration of one or more gases in the sample based on the electrical signals; and
an alarm that is generated in response to the gas concentration of a certain gas being in excess of a threshold.

16. The alarm system of claim 15, wherein the processor is configured to control the MEMS micro-mirror to direct the selected wavelengths of the light to the single detection point via the blazed grating.

17. The alarm system of claim 16, wherein the one of the selected wavelengths of the light corresponds to an absorption spectrum of one or more gases in the sample that are to be monitored.

18. The alarm system of claim 17, wherein the gas being monitored includes methane, and the one of the selected wavelengths of the light corresponds to the absorption spectrum of methane.

19. The alarm system of claim 15, wherein the detector includes an InGaAs single point detection device.

20. The alarm system of claim 15, wherein the alarm includes a visual alarm or an audio alarm.

* * * * *

UNITED STATES PATENT AND TRADEMARK OFFICE
CERTIFICATE OF CORRECTION

PATENT NO.        : 8,648,731 B2                                    Page 1 of 1
APPLICATION NO.   : 13/132080
DATED             : February 11, 2014
INVENTOR(S)       : Su et al.

It is certified that error appears in the above-identified patent and that said Letters Patent is hereby corrected as shown below:

In the Claims

In Column 3, Line 63, delete "ND converter" and insert -- A/D converter --, therefor.

In Column 6, Line 22, delete "(ILLUMATE" and insert -- (ILLUMINATE --, therefor.

Signed and Sealed this
Fifteenth Day of July, 2014

Michelle K. Lee
*Deputy Director of the United States Patent and Trademark Office*